United States Patent
Fischer et al.

(10) Patent No.: US 6,890,175 B2
(45) Date of Patent: May 10, 2005

(54) COOLING SYSTEM FOR HAND-HELD CURING LIGHT

(75) Inventors: Dan E. Fischer, Sandy, UT (US); Bruce S. McLean, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 166 days.

(21) Appl. No.: 10/325,206

(22) Filed: Dec. 18, 2002

(65) Prior Publication Data

US 2004/0121281 A1 Jun. 24, 2004

(51) Int. Cl.[7] .................................................. A61C 1/00
(52) U.S. Cl. ........................................................ 433/29
(58) Field of Search ............................ 433/29; 362/804, 362/373

(56) References Cited

U.S. PATENT DOCUMENTS

| | | |
|---|---|---|
| 3,310,358 A | 3/1967 | Marcatili |
| 3,704,928 A | 12/1972 | Coombs et al. |
| 3,930,149 A | 12/1975 | French |
| 4,184,196 A | 1/1980 | Moret et al. |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. |
| 4,309,617 A | 1/1982 | Long |
| 4,348,180 A | 9/1982 | Schuss |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III |
| 4,682,950 A | 7/1987 | Dragan |
| 4,698,730 A | 10/1987 | Sakai et al. |
| 4,733,937 A | 3/1988 | Lia et al. |
| 4,836,782 A | 6/1989 | Gonser |
| 4,906,187 A | * 3/1990 | Amadera ...................... 433/80 |
| 4,935,665 A | 6/1990 | Murata |
| 4,948,215 A | 8/1990 | Friedman |
| 4,963,798 A | 10/1990 | McDermott |
| 4,975,055 A | * 12/1990 | LaPlante ...................... 433/82 |
| 4,992,045 A | 2/1991 | Beisel |
| 5,013,144 A | 5/1991 | Silverglate et al. |
| 5,013,240 A | 5/1991 | Bailey et al. |
| 5,017,140 A | 5/1991 | Ascher |
| 5,043,634 A | 8/1991 | Rothwell, Jr. et al. |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |
| 5,161,879 A | 11/1992 | McDermott |
| 5,275,564 A | 1/1994 | Vassiliadis et al. |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. |
| 5,348,552 A | 9/1994 | Nakajima et al. |
| 5,371,826 A | 12/1994 | Friedman |
| 5,382,799 A | 1/1995 | May |

(Continued)

Primary Examiner—Cary E. O'Connor
(74) Attorney, Agent, or Firm—Workman Nydegger (57) ABSTRACT

A cooling system suitable for use with a light curing device includes a forced air unit, such as a diaphragm pump, a fan, or an eccentric cam blower that is disposed remotely from the hand-held portion of the light curing device, such as, within a power plug of the light curing device. Tubing electrically and pneumatically interconnects the power plug and the hand-held portion of the light curing device. Air blown by the forced air unit through the tubing is directed to the hand-held portion of the light curing device about a heat sink that is disposed therein. The circulating air displaces hotter air surrounding the heat sink, thereby lowering the ambient temperature within the light curing device.

18 Claims, 3 Drawing Sheets

U.S. PATENT DOCUMENTS

| | | |
|---|---|---|
| 5,388,988 A | 2/1995 | Goisser et al. |
| 5,397,892 A | 3/1995 | Abdelqader ............ 250/227.24 |
| 5,415,543 A | 5/1995 | Rozmajzl, Jr. |
| 5,420,768 A | 5/1995 | Kennedy |
| D361,382 S | 8/1995 | Brunsell et al. |
| 5,448,323 A | 9/1995 | Clark et al. |
| 5,457,611 A | 10/1995 | Verderber |
| 5,485,317 A | 1/1996 | Perissinotto et al. |
| 5,521,392 A | 5/1996 | Kennedy et al. |
| 5,527,261 A | 6/1996 | Monroe et al. |
| 5,616,141 A | 4/1997 | Cipolla |
| 5,634,711 A * | 6/1997 | Kennedy et al. ............ 362/119 |
| 5,660,461 A | 8/1997 | Ignatius et al. |
| 5,669,769 A | 9/1997 | Disel |
| D385,051 S | 10/1997 | Wu |
| D385,630 S | 10/1997 | Lieb et al. |
| 5,698,866 A | 12/1997 | Doiron et al. |
| 5,711,665 A | 1/1998 | Adam et al. |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,791,898 A | 8/1998 | Maissami |
| 5,797,740 A | 8/1998 | Lundvik |
| 5,803,729 A | 9/1998 | Tsimerman |
| 5,880,839 A | 3/1999 | Ishizuka et al. |
| 5,885,082 A | 3/1999 | Levy |
| 5,905,268 A | 5/1999 | Garcia et al. |
| 5,908,294 A | 6/1999 | Schick et al. |
| 5,908,295 A | 6/1999 | Kawata |
| 5,912,470 A | 6/1999 | Eibofner et al. |
| 5,921,777 A | 7/1999 | Dorman |
| 5,971,755 A | 10/1999 | Liebermann et al. |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. ............ 362/573 |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. ................. 433/29 |
| 6,155,823 A | 12/2000 | Nagel |
| 6,159,005 A | 12/2000 | Herold et al. |
| 6,200,134 B1 | 3/2001 | Kovac et al. ................. 433/29 |
| 6,208,788 B1 | 3/2001 | Nosov |
| 6,270,343 B1 | 8/2001 | Martin |
| 6,280,187 B1 | 8/2001 | Slone |
| 6,282,013 B1 | 8/2001 | Ostler et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao ............ 433/29 |
| 6,361,192 B1 | 3/2002 | Fussell et al. |
| 6,361,489 B1 | 3/2002 | Tsai |
| 6,390,815 B1 * | 5/2002 | Pond ............ 433/80 |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,439,888 B1 | 8/2002 | Boutoussov et al. |
| 6,465,961 B1 | 10/2002 | Cao |
| 6,468,077 B1 | 10/2002 | Melikechi et al. |
| 6,478,447 B2 | 11/2002 | Yen |
| 6,482,004 B1 | 11/2002 | Senn et al. |
| 6,485,301 B1 | 11/2002 | Gemunder et al. |
| 6,511,317 B2 | 1/2003 | Melikechi et al. |
| 6,511,321 B1 | 1/2003 | Trushkowsky et al. |
| 6,514,075 B1 | 2/2003 | Jacob |
| 6,611,110 B1 | 8/2003 | Fregoso |
| 6,659,768 B1 * | 12/2003 | Ito et al. ............ 433/95 |
| 6,692,251 B1 | 2/2004 | Logan et al. |
| 6,692,252 B2 | 2/2004 | Scott |
| 6,709,128 B2 | 3/2004 | Gordon et al. |
| 6,719,558 B2 | 4/2004 | Cao |
| 6,719,559 B2 | 4/2004 | Cao |
| 6,755,648 B2 | 6/2004 | Cao |
| 6,755,649 B2 | 6/2004 | Cao |
| 2001/0038992 A1 | 11/2001 | Otsuka |
| 2001/0046652 A1 | 11/2001 | Ostler et al. ............ 433/29 |
| 2001/0055451 A1 | 12/2001 | Kuhara et al. |
| 2002/0073921 A1 | 6/2002 | Russell et al. ............ 118/620 |
| 2002/0085372 A1 | 7/2002 | Lehrer |
| 2002/0093833 A1 | 7/2002 | West |
| 2002/0115037 A1 | 8/2002 | Cao ............ 433/29 |
| 2002/0133970 A1 | 9/2002 | Gordon et al. |
| 2002/0147383 A1 | 10/2002 | Weber et al. |
| 2002/0163317 A1 | 11/2002 | Cao |
| 2002/0167283 A1 | 11/2002 | Cao |
| 2002/0168306 A1 | 11/2002 | Cao |
| 2002/0168604 A1 | 11/2002 | Cao ............ 433/29 |
| 2002/0168605 A1 | 11/2002 | Cao |
| 2002/0168606 A1 | 11/2002 | Cao |
| 2002/0168607 A1 | 11/2002 | Cao |
| 2002/0168608 A1 | 11/2002 | Cao |
| 2002/0172912 A1 | 11/2002 | Cao ............ 433/29 |
| 2002/0172913 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao ............ 433/29 |
| 2002/0172917 A1 | 11/2002 | Cao |
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao ............ 392/409 |
| 2002/0182561 A1 | 12/2002 | Cao |
| 2002/0182562 A1 | 12/2002 | Cao |
| 2002/0187454 A1 | 12/2002 | Melikechi et al. |
| 2002/0187455 A1 | 12/2002 | Melikechi et al. |
| 2002/0190659 A1 | 12/2002 | Cao |
| 2002/0190660 A1 | 12/2002 | Cao |
| 2002/0197582 A1 | 12/2002 | Cao ............ 433/29 |
| 2003/0001507 A1 | 1/2003 | Cao ............ 315/56 |
| 2003/0036031 A1 | 2/2003 | Lieb et al. |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1 * | 5/2003 | Becker ............ 362/573 |
| 2003/0133203 A1 | 7/2003 | McLean et al. |
| 2003/0133298 A1 | 7/2003 | Cao |
| 2003/0142413 A1 | 7/2003 | McLean et al. |

| | | | | | |
|---|---|---|---|---|---|
| 2003/0147254 A1 | 8/2003 | Yoneda et al. | 2003/0218880 A1 | 11/2003 | Brukilacchio |
| 2003/0147258 A1 | 8/2003 | Fischer et al. | 2003/0219693 A1 | 11/2003 | Cao |
| 2003/0148242 A1 | 8/2003 | Fischer et al. | 2003/0219694 A1 | 11/2003 | Bianchetti et al. |
| 2003/0152885 A1 | 8/2003 | Dinh | 2003/0235800 A1 | 12/2003 | Qadar |
| 2003/0173720 A1 * | 9/2003 | Musso et al. ............... 264/635 | 2004/0033033 A1 | 2/2004 | Hoshino et al. |
| 2003/0186195 A1 | 10/2003 | Comfort et al. | | | |
| 2003/0215766 A1 | 11/2003 | Fischer et al. | * cited by examiner | | |

COOLING SYSTEM FOR HAND-HELD CURING LIGHT

BACKGROUND OF THE INVENTION

1. The Field of the Invention

The present invention is in the field of light curing devices and, more particularly, in the field pneumatic cooling systems configured to cool hand-held light curing devices.

2. The Relevant Technology

In the field of dentistry, dental cavities are often filled and sealed with photosensitive compounds that are cured by exposure to radiant light energy. These compounds, commonly referred to as light-curable compounds, are placed within dental cavity preparations or onto dental surfaces where they are subsequently irradiated by light. The light is typically generated by a light curing device with a lamp such as a halogen lamp bulb, a light-emitting diode (LED), a plurality of LEDs, or an LED array. The light that radiates from the light curing device is emitted directly within the mouth of a patient or it is channeled into the mouth of a patient with an appropriate light guide. The emitted light causes photosensitive components within the photosensitive compounds to polymerize, thereby hardening the compounds within the patient's mouth.

One problem experienced with existing light curing devices, however, is that the incorporated light sources (e.g., lamps, LED, or LED array) generate heat that is typically undesired. The heat generated by the light curing devices is generally undesired because it can potentially create discomfort to the patient, such as when the light curing device happens to come in contact or immediate proximity with the sensitive mouth tissues of the patient. Heat generated by the light curing device can also create discomfort for the practitioner who is holding the light curing device. Accordingly, it is generally desirable to minimize the heat of the light curing device during use.

One method for minimizing the heat of a light curing device is to use heat sinks that are configured to dissipate the heat. For example, the light source(s) of the light curing device can be mounted on a heat sink, in contact with a heat sink, or in close proximity to a heat sink. Heat sinks, which operate on the principles of conduction and convention, are well known in the art of thermodynamics.

To further increase the ability of a heat sink to diffuse heat, certain existing light curing devices have been equipped with a fan that is disposed within the housing of the light curing device and that is configured to blow air over the heat sink, as disclosed in U.S. Pat. No. 6,200,134, to Kovac et al. Although the fan helps to dissipate the heat generated by the light curing device, the added size and weight of the fan can increase the overall size and weight of the light curing device.

SUMMARY OF THE INVENTION

Briefly summarized, the embodiments of the present invention are directed to pneumatic systems that are configured to cool hand-held curing lights.

According to one aspect of the invention, the cooling system includes a forced air unit, such as a fan, an eccentric cam blower, or a diaphragm pump, that is located remotely from the hand-held portion of the light curing device. The forced air unit is in fluid communication with the light curing device and is configured to circulate air within the hand-held portion of the light curing device.

According to one embodiment, the forced air unit is physically disposed within the power supply plug of the light curing device, remotely located from the housing of the light curing device. According to this embodiment, tubing interconnects the forced air unit and the hand-held portion of the light curing device. Air is able to flow through the tubing between the forced air unit and the hand-held portion of the light curing device.

The tubing may comprise any suitable tubing including, but not limited to, standard four-hole tubing that is used in the dental industry to supply power and air to dental hand pieces such as high speed turbines, low speed turbines, drills, and so forth. Four-hole tubing is especially practical because the electrical wiring between the light curing device and a remote power supply can also be contained within the four-hole tubing. Nevertheless, it will be appreciated that the invention is not limited to the use of four-hole tubing. It will also be appreciated that the tubing may comprise any desired length, although, according to one embodiment, the length of the tubing is approximately 8 feet to 10 feet in length.

The forced air unit is configured to generate a supply of pressurized air that is sufficient to blow air through the tubing and to circulate the air about a heat sink that is disposed within the hand-held portion of the light curing device. According to one embodiment, the forced air unit is configured to generate a supply of pressurized air having a pressure of between about 20 psi and about 30 psi.

The heat sink that is disposed within the light curing device may be configured as a solid structure or as a hollow structure. For embodiments in which the heat sink comprises a solid structure, the pressurized air is circulated around the exterior of the heat sink. For embodiments in which the heat sink comprises a hollow structure, the pressurized air is circulated through the hollow portions of the heat sink. In certain embodiments, the air may also be circulated both through and around the heat sink. As the air is circulated about the heat sink, the hot air previously surrounding the heat sink is displaced, thereby lowering the ambient temperature surrounding the heat sink and within the light curing device. The displaced hot air is directed into exhaust tubing that is configured to carry the hot air away from the light curing device.

In summary, the present invention provides a remote pneumatic cooling system that is capable of circulating air around and/or through a heat sink to increase the ability of the heat sink to dissipate the heat that is generated by a light curing device. Inasmuch as the forced air unit is located remotely from the housing of the light curing device, the overall weight and size of the hand-held portion of the light curing device is not undesirably augmented by the cooling system of the invention.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the invention will now be provided with specific reference to figures illustrating preferred embodiments of the invention. It will be appreciated that like structures will be provided with like reference designations. To provide context for interpreting the scope of the invention, certain terms used throughout the application will now be defined.

The term "fluid communication," which is used herein to characterize a relationship between certain components of the cooling system, refers to a state in which air can controllably flow between the components that are said to be in fluid communication. According to one embodiment, for example, a remotely located forced air unit is in fluid communication with a light curing device, such that air is able to controllably flow between the forced air unit and the light curing device.

The term "forced air unit," as used herein, refers to any device that is capable of generating a supply of pressurized air or that is otherwise capable of forcing air through air channels or tubing. Non-limiting examples of forced air units include fans and eccentric cam blowers. Eccentric cam blowers, which are well known in the art of pumps and air blowing devices, utilize an eccentric cam to compress and retract one or more bellows to create a desired airflow. Diaphragm pumps, which are also well known in the art of pumps, can also be used to create a desired flow of pressurized air according to the invention.

In general, the cooling systems of the invention, as described herein, each include a remotely located forced air unit that is configured to circulate air about a heat sink that is disposed within the hand-held portion of a light curing device. The term "hand-held portion" refers to the portion of the light curing device that is held in the hand of the practitioner. The hand-held portion may also include the portion of the light curing device that is inserted within a patient's mouth. The term "hand-held portion of the light curing device" is also used interchangeably with the term "housing of the light curing device."

According to one embodiment, the air circulated by the cooling system of the invention displaces the hot air residing around the heat sink, thereby lowering the ambient temperature within the hand-held portion of the light curing device. According to one embodiment, the forced air unit is not disposed within the hand-held portion of the light curing device, but is instead located in a remote location, such as a power plug, thereby reducing the number of components that are contained within the hand-held portion of the light curing device.

Figure 1:
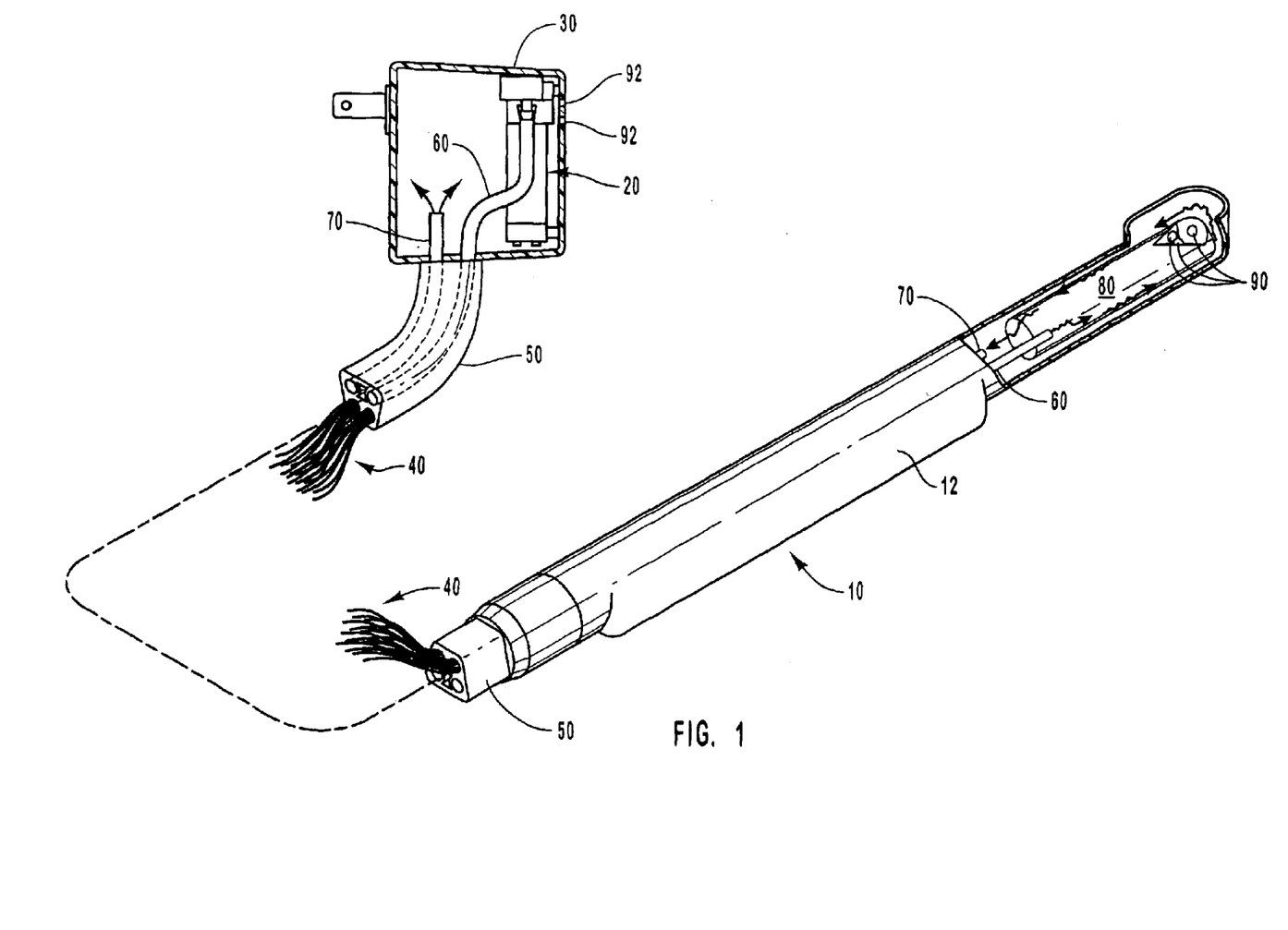
FIG. 1 illustrates one embodiment of the cooling system of the invention integrated within a light curing device, in which a forced air pump is disposed within the power plug of the light curing device, a heat sink is disposed within the hand-held portion of the light curing device, and tubing interconnects the power plug and the hand-held portion of the light curing device.

FIG. 1 illustrates one embodiment of the cooling system of the invention that is integrated into a light curing device 10. As described herein, the cooling system of the invention is configured to help lower the temperatures of the hand-held portion 12 of the light curing device 10. The present embodiment of the cooling system includes a forced air unit 20 that is located remotely from the hand-held portion 12 of the light curing device 10. The forced air unit 20 may include a fan, an eccentric cam, a diaphragm pump (as shown), or any other device that is configured to generate a supply of pressurized air.

According to the present embodiment, the forced air unit 20 is disposed within the housing of the power plug 30 of the light curing device 10. This configuration is particularly useful because it enables the forced air unit 20 to be consolidated within existing components of the light curing device 10, namely, the power plug 30, without unnecessarily increasing the size and weight of the hand-held portion 12 of the light curing device 10.

In the present illustration, the electrical circuitry and wiring of the power plug 30 is not shown so that the components of the cooling system 30 can be more clearly seen and emphasized. It will be appreciated, however, that the power plug 30 includes sufficient standard electronic circuitry and wiring to enable the power plug 30 to electrically couple with a remote power supply and to provide an adequate supply of power to the light curing device 10 for operation when the power plug 30 is electrically coupled with the remote power supply. Examples of remote power supplies include standard electrical wall receptacles, batteries and generators.

As shown, the power plug 30 is electrically connected to the light curing device 10 with wires 40 that extend from the power plug 30 to the hand-held portion 12 of the light curing device 10. The wires 40 may be contained within a cord or specialized tubing, such as the four-hole tubing 50 that is illustrated. Four-hole tubing is a standard component available in the dental industry and is often used to supply power to and air to hand pieces such as turbines and drills.

The four-hole tubing 50 is particularly useful in the present embodiment because it can be used to interconnect the forced air unit 20 with the light curing device both electrically and pneumatically, as shown. In particular, one of the tubes formed in the four-hole tubing can be used as an air supply line 60 to supply air from the forced air unit to the hand-held portion 12 of the light curing device 10. Another tube formed in the four-hole tubing can also be used as an air exhaust line 70 for removing air that has been displaced from the hand-held portion of the light curing device 10, as described in more detail below. In one embodiment, the length of the tubing 50 between the power plug 30 and the hand-held portion 12 of the light curing device 10 is between about 5 feet and about 15 feet. However, the length of the tubing 40 may comprise any desire length.

During use, the forced air unit 20 creates a supply of pressurized air that is sufficient to circulate air through the tubing 50 and about the heat sink 80 which is disposed within the hand-held portion of the light curing device 10. According to one embodiment, the forced air unit is configured to generate a supply of air that has a pressure of between about 20 psi and about 30 psi. However, it will be appreciated that the amount of pressure that is required to circulate the air through the cooling system of the invention is dependent upon several factors including, but not limited to, the size and length of the tubing as well as the configuration of the heat sink. Accordingly, the forced air unit 20 may also be configured to generate pressurized air having pressures of less than 20 psi and greater than 30 psi.

As illustrated, the pressurized air is directed through the air supply line 60 to the hand-held portion 12 of the light curing device 10, where the air is ultimately expelled and forced to circulate about the heat sink 80. As the air circulates about the heat sink 80, the air displaces hotter air surrounding the heat sink 80. This helps the heat sink 80 to diffuse the heat that is generated by the light source of the light curing device 10. In the present embodiment, the light source comprises a plurality of LEDs that are mounted to the heat sink. However, it will be appreciated that the invention is not limited to embodiments in which the light source of the light curing device comprises LEDs, or to embodiments in which the light source is mounted directly to the heat sink.

The air that is circulated about the heat sink 80 is finally expelled through the air exhaust line 70 that is configured to direct the hot air away from the hand-held portion 12 of the light curing device 10. In one embodiment, the air exhaust line 70 channels the air all the way back to the power supply plug 30 where the air is vented out of small holes or cracks natural occurring within the power supply plug 30. The air can also be vented out of small holes that are intentionally manufactured 92 into the power supply plug 30.

Figures 2, 3:
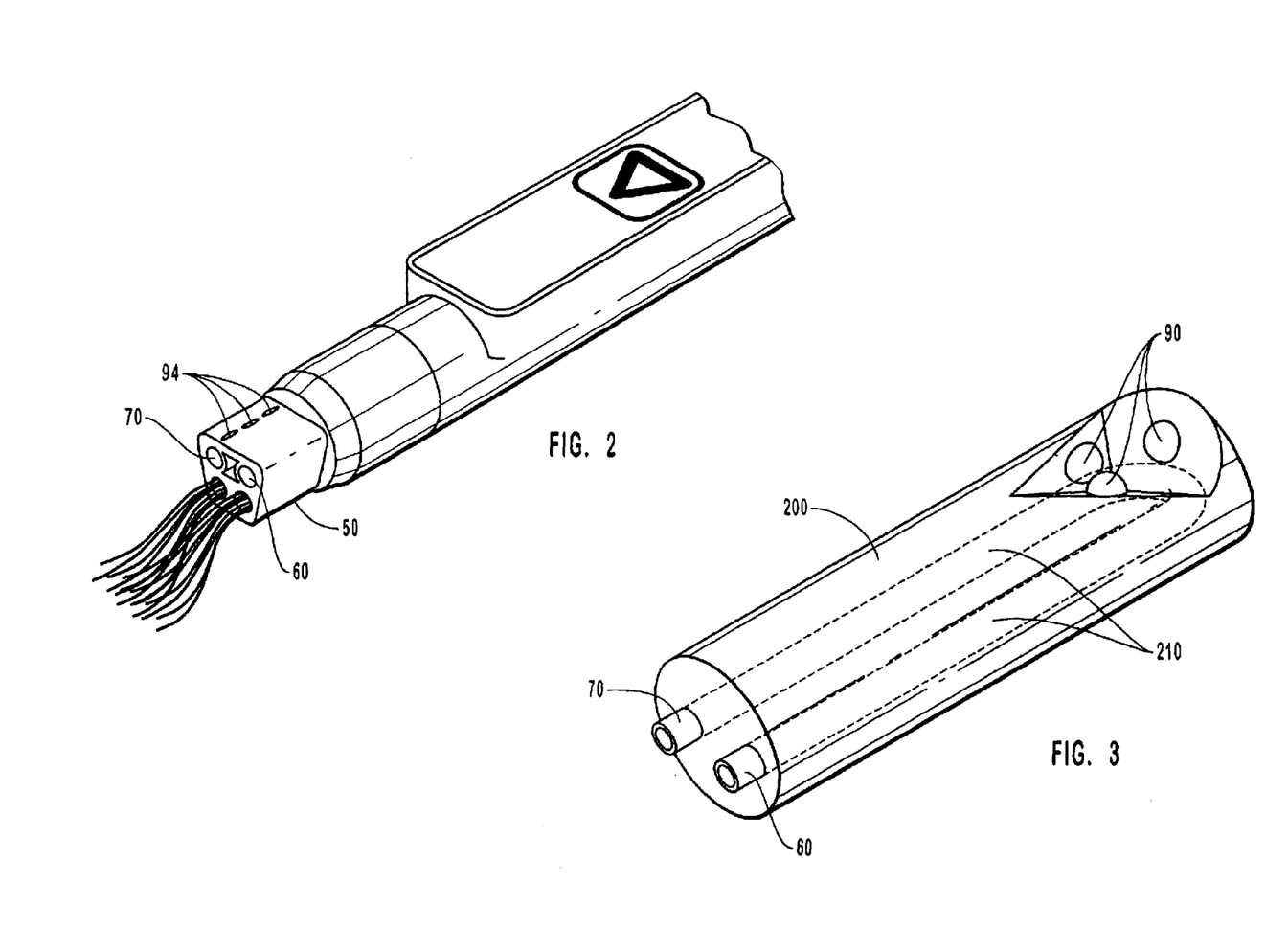
FIG. 2 illustrates one embodiment of four-hole tubing in which vents are formed into the tubing to allow air to escape from the tubing.
FIG. 3 illustrates one embodiment of a heat sink that has an air passage formed into the body of the heat sink.

FIG. 2 illustrates another embodiment in which the air that is forced into the air exhaust line 70 can be vented out of exhaust line 70 through small holes 94 that are formed directly into the four-hole tubing 50. This embodiment may be preferred to reduce the amount of pressure required to circulate the air through the tubing. This can also be useful to prevent hot air from circulating back to the power supply plug 30.

Although the examples provided above describe how the cooling-system is designed to circulate air about or around the heat sink 80, it will be appreciated that the cooling-system may also include a heat sink that is hollow so that the air can flow directly through the heat sink. By way of example, and not limitation, FIGS. 3 and 4 illustrate embodiments of heat sinks that are hollow that can be included with the cooling systems of the invention.

FIG. 3 illustrates one embodiment of a hollow heat sink 200 that includes a hollow channel 210 having two ends that is formed into the heat sink 200. In this embodiment, the air supply line 60 is fed into one end of the hollow channel 210, thereby enabling the pressurized air to flow into the hollow channel 210. During use, the air flows through the hollow channel 210 and into the air exhaust line 70 where it is finally directed away from the heat sink 200. It will be appreciated that as the air flows through the hollow channel 210 it lowers the temperature of the heat sink by displacing hotter air that resided within the hollow channel 210.

The hollow channel 210 is shown in the present embodiment to extend through substantially the entire length of the heat sink 200. This embodiment is useful because it allows the air to flow past the portion of the heat sink 200 that is mounting the heat generating light sources (e.g., the LEDs 90). Accordingly, this can help accelerate the diffusion of any heat generated by the LEDs 90. It will be appreciated, however, that the cooling system of the invention may also include a heat sink that is configured with one or more hollow channels that pass through only a limited portion of the heat sink.

Figure 4:
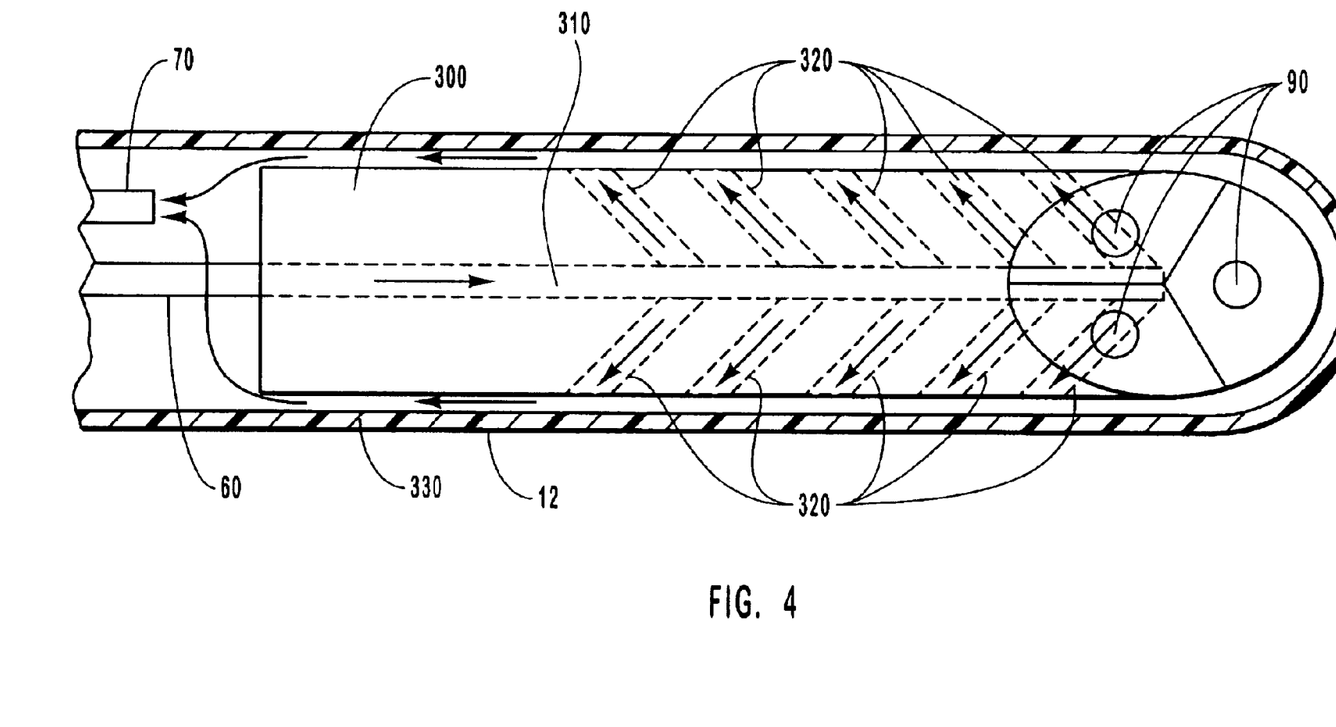
FIG. 4 illustrates one embodiment of a heat sink within the housing of a light curing device in which the heat sink has internal air channels and sub-channels formed into the body of the heat sink.

FIG. 4 illustrates another embodiment of a hollow heat sink 300 that may be included as part of the cooling system of the invention. In this embodiment, the heat sink 300 is configured with a hollow channel 310 that passes through the center of the heat sink and a plurality of sub-channels 320 that extend from the hollow channel 310 to the exterior of the heat sink 300. According to this embodiment, the air supply line 60 is fed into the hollow channel 310 but, unlike the previous embodiment, the air exhaust line 70 is not connected with the heat sink 300. Rather, the air exhaust line 70 is separated from the heat sink 300 so that the air that is forced through the hollow channel 310 first passes through the sub-channels 320 and along the side of the heat sink 300 before it ultimately flows into the air exhaust line 70, where it is directed away from the heat sink 300. In particular, as the air is forced out of the sub-channels 320, the air is forced through the gap existing between the heat sink 300 and the housing 330 of the light curing device until it arrives at the air exhaust line 70. This embodiment is particularly useful because it allows the air to flow both through the heat sink 300 and around the heat sink 300. This effectively increases the surface area of the heat sink 300 over which the air is able to flow while providing a cooling effect.

Although the embodiments described above all make reference to an air exhaust line 70, it will be appreciated that the invention is not limited to embodiments that include an air exhaust line. In particular, the light curing devices can be configured with small ports or holes through which the air can escape upon circulating about the heat sink.

Control over operation of the cooling system vary to accommodate different needs and preferences and is not critical to the scope of the invention. In particular, control over the operation of the cooling system may be integrated with operation of the light curing device, such that the cooling system is operated whenever the light curing device is operated. Alternatively, the cooling system may comprise individual controls for operating the cooling system independent of the light curing device. The cooling system may also be configured to operate whenever the power plug 30, described above in reference to FIG. 1, is plugged in.

In summary, the cooling system of the invention, as described above, includes a remotely located forced air unit that is configured to circulate air about a heat sink that is disposed within a light curing device. The circulating air displaces the hot air residing around the heat sink. The forced air unit is not disposed within the housing of the light curing device, but is instead remotely located from the housing of the light curing device, thereby reducing the number of components that are contained within the housing of the light curing device. It will be appreciated that this is an improvement over existing devices in the art.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A cooling system for a light curing device, wherein the light curing device includes a hand-held portion that is configured to generate and emit light and a power plug that is configured to electrically couple with a remote power supply, and wherein the cooling system is configured to lower the temperature of the hand-held portion of the light curing device, the cooling system comprising:

a forced air unit configured to generate a supply of pressurized air, the forced air unit being disposed within the power plug of the light curing device; and tubing pneumatically interconnecting the forced air unit with the hand-held portion of the light curing device, such that operation of the forced air unit causes air to circulate through the tubing to the hand-held portion of the light curing device, wherein air circulating to the hand-held portion of the light curing device through the tubing helps to lower an ambient temperature of the hand-held portion of the light curing device.

2. A cooling system as recited in claim 1, further comprising a heat sink disposed within the hand-held portion of the light curing device, the heat sink being configured to diffuse heat generated by a light source disposed at the hand-held portion of the light curing device.

3. A cooling system as recited in claim 2, the tubing being configured to direct circulated air about the heat sink such that the circulating air is able to lower an ambient temperature surrounding the heat sink.

4. A cooling system as recited in claim 3, the heat sink comprising a solid structure such that circulated air is forced to circulate around an exterior of the heat sink.

5. A cooling system as recited in claim 3, the heat sink comprising a hollow structure having a hollow channel formed therein, and wherein the tubing is configured to direct circulated air through the hollow channel formed in the heat sink.

6. A cooling system as recited in claim 3, the heat sink comprising a hollow structure having a hollow channel and a plurality of sub-channels formed therein, and wherein the tubing is configured to direct circulated air through the hollow channel and the plurality of sub-channels formed in the heat sink.

7. A cooling system as recited in claim 3, the light curing device comprising a light source mounted adjacent the heat sink.

8. A cooling system as recited in claim 1, the forced air unit comprising a diaphragm pump.

9. A cooling system as recited in claim 1, the forced air unit comprising a fan.

10. A cooling system as recited in claim 1, the forced air unit comprising an eccentric cam blower.

11. A cooling system as recited in claim 1, the tubing comprising an air supply line for supplying air to the hand-held portion of the light curing device from the forced air unit and an air exhaust line for directing displaced air away from the hand-held portion of the light curing device.

12. A cooling system as recited in claim 11, the air exhaust line circulating displaced air away from the light curing device.

13. A cooling system as recited in claim 11, the tubing being configured to carry electrical wires from the power plug to the hand-held portion of the light curing device.

14. A cooling system as recited in claim 13, the tubing comprising four-hole tubing.

15. A cooling system as recited in claim 11, the exhaust line comprising vents for discharging displaced air from the vents formed in the tubing.

16. A cooling system as recited in claim 1, the forced air unit being configured to generate a supply of pressurized air having a pressure of between about 2 psi and about 30 psi.

17. A cooling system in combination with a light curing device, the light curing device comprising a hand-held portion that is configured to generate and emit light and a power plug that is configured to electrically couple with a remote power supply, the cooling system being configured to lower the temperature of the hand-held portion of the light curing device, the cooling system comprising:

a diaphragm pump disposed within the power plug of the light curing device, the diaphragm pump being configured to generate a supply of pressurized air;

a heat sink disposed within the hand-held portion of the light curing device, the heat sink being configured to diffuse heat generated by a light source disposed within the hand-held portion of the light curing device; and tubing pneumatically interconnecting the forced air unit with the hand-held portion of the light curing device, such that operation of the forced air unit causes air to circulate through the tubing to the hand-held portion of the light curing device, the tubing directing the air to circulate about the heat sink, such that the circulating air helps to lower an ambient temperature surrounding the heat sink within the hand-held portion of the light curing device.

18. A cooling system for a light curing device, wherein the light curing device includes a hand-held portion that is configured to generate and emit light and a power plug that is configured to electrically couple with a remote power supply, and wherein the cooling system is configured to lower the temperature of the hand-held portion of the light curing device, the cooling system comprising:

a forced air unit configured to generate a supply of pressurized air, the forced air unit being disposed remotely from the hand-held portion of the light curing device; and tubing pneumatically interconnecting the forced air unit with the hand-held portion of the light curing device, such that operation of the forced air unit causes air to circulate through the tubing to the hand-held portion of the light curing device, the tubing comprising an air supply line for supplying air to the hand-held portion of the light curing device from the forced air unit and an air exhaust line for directing displaced air away from the hand-held portion of the light curing device, the exhaust line comprising vents for discharging displaced air from the vents formed in the tubing;

wherein air circulating to the hand-held portion of the light curing device through the tubing helps to lower an ambient temperature of the hand-held portion of the light curing device.

* * * * *

UNITED STATES PATENT AND TRADEMARK OFFICE
CERTIFICATE OF CORRECTION

PATENT NO.    : 6,890,175 B2
DATED         : May 10, 2005
INVENTOR(S)   : Dan E. Fischer and Bruce S. McLean It is certified that error appears in the above-identified patent and that said Letters Patent is hereby corrected as shown below:

<u>Column 4,</u>
Line 60, change "40" to -- 50 --.

Signed and Sealed this

Twenty-third Day of August, 2005

JON W. DUDAS
*Director of the United States Patent and Trademark Office*